United States Patent [19]

Aszalos et al.

[11] Patent Number: 5,468,469
[45] Date of Patent: Nov. 21, 1995

[54] METHODS OF USING AZO DYES AND THEIR DERIVATIVES

[75] Inventors: Adorjan Aszalos, Bethesda; James L. Weaver, Gaithersburg; P. Scott Pine, Rockville, all of Md.

[73] Assignee: The United States of America as represented by the Department of Health and Human Services, Washington, D.C.

[21] Appl. No.: 203,654

[22] Filed: Feb. 28, 1994

Related U.S. Application Data

[63] Continuation of Ser. No. 930,315, Aug. 11, 1992, abandoned.

[51] Int. Cl.⁶ .................................................. G01N 1/00
[52] U.S. Cl. .................... 514/150; 435/7.24; 435/240.2
[58] Field of Search ............................... 514/150; 424/2, 424/7.1

[56] References Cited

U.S. PATENT DOCUMENTS

| | | | |
|---|---|---|---|
| 662,122 | 11/1900 | Israel et al. | 534/828 |
| 663,498 | 12/1900 | Israel et al | 534/828 |

FOREIGN PATENT DOCUMENTS 0287909  10/1988  European Pat. Off. .

OTHER PUBLICATIONS

Alarcón et al., *Antiviral Research*, 4, 231–243 (1984).
Anand et al., *Antimicrobial Agents and Chemotherapy*, 32(5), 684–688 (May 1988).
Anand et al., *Antiviral Chemistry & Chemotherapy*, 1(1), 41–46 (1990).
Cushman et al., *J. Med. Chem.*, 34, 337–342 (1991).
Lifson et al., *Science*, 241, 712–716 (Aug. 5, 1988).
Smith et al., *Science*, 238, 1704–1707 (Dec. 18, 1987).
Åkerfeldt et al., "Aromatic Sulfonic Acids as Viral Inhibitors. Structure–Activity Study using Rhino, Adeno 3, Herpes Simplex, and Influenza Viruses," *J. Medicin. Chem.*, 14(7), 596–600 (1971).
Anand et al., "Sodium Pentosan Polysulfate (PPS), an Anti–HIV Agent Also Exhibits Synergism with AZT, Lymphoproliferative Activity,a nd Virus Enhancement," *AIDS Res. Human Retrovir.*, 6, 679–689 (1990).
Balzarini et al., "Aurintricarboxylic Acid and Evans Blue Represent Two Different Classes of Anionic Compounds Which Selectively Inhibit the Cytopathogenicity of Human T–Cell Lymphotropic Virus Type III/Lymphadenopathy–Associated Virus," *Biochem. Biophys. Res. Commun.*, 136, 64–71 (1986).
Balzarini et al., "Comparative Inhibitory Effects of Suramin and Other Selected Compounds on the Infectivity and Replication of Human T–Cell Lymphotropic Virus (HTLV–III)/Lymphadenopathy–Associated Virus (LAV)," *Int. J. Cancer*, 37, 451–457 (1986).
Cushman et al., "Preparation and Anti–HIV Activities of Aurintricarboxylic Acid Fractions and Analogues: Direct Correlation of Antiviral Potency with Molecular Weight," *J. Med. Chem.*, 34, 329–337 (1991).
Hurst et al., "The Prevention of Encephalitis Due To The Viruses of Eastern Equine Encephalomyelitis and Louping–Ill: Experiments with Trypan Red, Mepacrine, and Many Other Substances," *Brit. J. Pharmacol.*, 7, 455–472 (1952).
Mohan et al., "Potential Anti–AIDS Agents. Synthesis and Antiviral Activity of Naphthalenesulfonic Acid Derivatives against HIV–1 and HIV–2," *J. Med. Chem.*, 34, 212–217 (1991).
Pal et al., "Comparative Effects of Polyanionic Compounds on Syncytia Formation and Infectivity of Human Immunodeficiency Virus Type I and Type II," *Aids Res. Human Retrovir.*, 7, 133 (1991).
Thorne et al., "Inactivation of Measles and Herpes Simplex Viruses by Trypan Blue," *J. Gen. Virol.*, 64, 1365–1368 (1983).
Weaver et al., "Polyionic Compounds Selectively Alter Availability of CD4 Receptors for HIV Coat Protein rgp120," *AIDS Res. Human Retrovir.*, 6, 1125–1130 (1990).
Weaver et al., "Inhibition of the binding of HIV rgp120 to CD4 by dyes," *Antiviral Chem. & Chemotherapy*, 3(3), 147–151 (1992).

*Primary Examiner*—Russell Travers
*Attorney, Agent, or Firm*—Leydig, Voit & Mayer, Ltd.

[57] ABSTRACT

Pharmaceutical compositions containing the azo dyes Direct Orange 26, Direct Red 23, Direct Red 24, Direct Red 26, and similar dyes, as well as the use of such azo dyes to inhibit the binding of a virus to the CD4 glycoprotein, in detecting or quantitating CD4-positive T4 lymphocytes, and in the protection against or treatment of viral infections.

15 Claims, 1 Drawing Sheet

METHODS OF USING AZO DYES AND THEIR DERIVATIVES

This is a continuation of application Ser. No. 07/930,315 filed on Aug. 11, 1992, now abandoned.

FIELD OF THE INVENTION

The present invention relates to pharmaceutical azo dye compositions and methods for their use. In particular, this invention relates to pharmaceutical compositions containing the azo dyes Direct Orange 26, Direct Red 23, Direct Red 24, Direct Red 26, derivatives thereof, and structurally related compounds. These compositions are useful in inhibiting the binding of a virus to the CD4 glycoprotein, in the protection or treatment of viral infections, particularly from human immunodeficiency virus, and in detecting and quantitating CD4-positive T4 lymphocytes.

BACKGROUND OF THE INVENTION

A variety of compounds have been investigated for their antiviral properties. For example, the dyes Trypan blue, Evans blue, Congo Red and derivatives thereof, as well as additional related compounds, have been examined as potential antiviral agents (Alarcon et al., *Antiviral Research,* 4, 231–243 (1984); Thorne et al., *J. Gen. Viral.,* 64, 1365–1368 (1983); Westin et al., *J. of Med. Chem.,* 14(7), 596–60 (1971); Mohan et al., *J. Med. Chem.,* 34, 212–217 (1991)). Several compounds which have been demonstrated to inhibit replication of the human immunodeficiency virus (HIV) include soluble CD4 protein and synthetic derivatives (Smith, D. H. et al., *Science,* 238, 1704–1707 (1987); Lifson et al., *Science,* 241, 712–716 (1988)), dextran sulfate (Ito et al., *Antivir Res.,* 7, 361–367 (1987)), and the dyes Direct Yellow 50 (Balzarini et al., *Int. J. Cancer,* 37, 451–457 (1986b)), aurintricarboxylic acid (ATA) and Evans Blue (EB) (Balzarini et al., *Biochem. Biophys. Res. Commun.,* 136, 64–71 (1986a)). Some of these antiviral agents have been shown to act by blocking binding of gp120, the coat protein of HIV, to its target, the CD4 glycoprotein of T4 lymphocytes (Smith, D. H. et al. *Science,* 238, 1704–1707 (1987); Lifson et al., *Science,* 241, 712–716 (1988); Weaver et al., *AIDS Res. Human Retrovir.,* 6, 1125–1130 (1990)). However, many of these pharmaceutical compounds, in particular the dyes Trypan blue and Congo Red, also mediate additional undesired effects at the cellular and organismic levels, such as induction of congenital abnormalities (Thorne et al., supra) or in vivo metabolism to carcinogens (Mohan et al., supra).

Other dyes hold more promise as pharmaceutical agents and, particularly, as antiviral agents. Recently, several azo dye derivatives, including Direct Red 79, Acid Blue 116, and Acid Red 115, were examined for their efficacy against HIV (U.S. patent application Ser. No. 07/684,258). Despite similarity in the general structure of the twenty-five azo dyes, only two-thirds of the disclosed azo dyes tested were found to be effective at impairing the binding of a CD4 monoclonal antibody (αCD4) to T4 lymphocytes. These results were similar to those obtained in earlier examinations of dye derivatives, which suggested that possession of certain structural features such as sulfonic acid groups (Akerfeldt et al., *J. Medicin. Chem.,* 14(7), 596–600, 1971) or a biphenyl spacer separating napthalenedisulfonic acid groups (Mohan et al., supra) might be important for binding to CD4, but failed to clearly define features critical for CD4 binding. It is evident that the present state-of-the-art does not allow a prediction of CD4 binding ability to be made for a compound merely as a result of it being an azo dye, or based upon possession of a particular chemical structure.

Additionally, the azo dyes described above which proved effective in inhibiting binding to CD4 all shared the disadvantage of demonstrating significant binding to serum proteins. Such binding limits the use of these dyes as antiviral agents, as it reduces ability to inhibit binding to CD4. Consequently, there remains a need for pharmaceutical agents that are capable of binding the CD4 glycoprotein of T4 lymphocytes, and that demonstrate reduced binding to serum proteins. It is an object of the present invention to provide pharmaceutical compositions containing azo dye derivatives which satisfy these criteria, and therefore demonstrate significant utility for the diagnosis, treatment, and prevention of viral diseases.

It is an additional object of the present invention to provide a method of inhibiting the binding of a virus to CD4-positive T4 lymphocytes, particularly with respect to a retrovirus, and more particularly as regards HIV. It is a further object of the present invention to provide a method of treating and protecting against viral infection, particularly with respect to a retrovirus, and more particularly as regards HIV. It is yet another object of the present invention to provide a diagnostic method of detecting CD4-positive T4 lymphocytes.

These and other objects and advantages of the present invention, as well as additional inventive features, will be apparent from the description of the invention provided herein.

BRIEF SUMMARY OF THE INVENTION

The present invention relates to pharmaceutical azo dye compositions and methods for their use. In particular, this invention relates to pharmaceutical compositions containing the azo dyes Direct Orange 26, Direct Red 23, Direct Red 24, Direct Red 26, derivatives of these dyes, and similar compounds. The azo dyes described herein possess similar structural features, namely substituted azonapthalene sulfonic acid groups separated by a carboxydiamide spacer, as well as the ability to inhibit the binding of the HIV coat protein gp120 to its target, CD4 glycoprotein present on peripheral blood lymphocytes. Thus these azo dyes are of use in inhibiting the binding of a virus to CD4, in the protection against and treatment of viral infections, and in detecting and quantitating CD4-positive lymphocytic cells.

DESCRIPTION OF THE PREFERRED EMBODIMENTS

Figure 1:
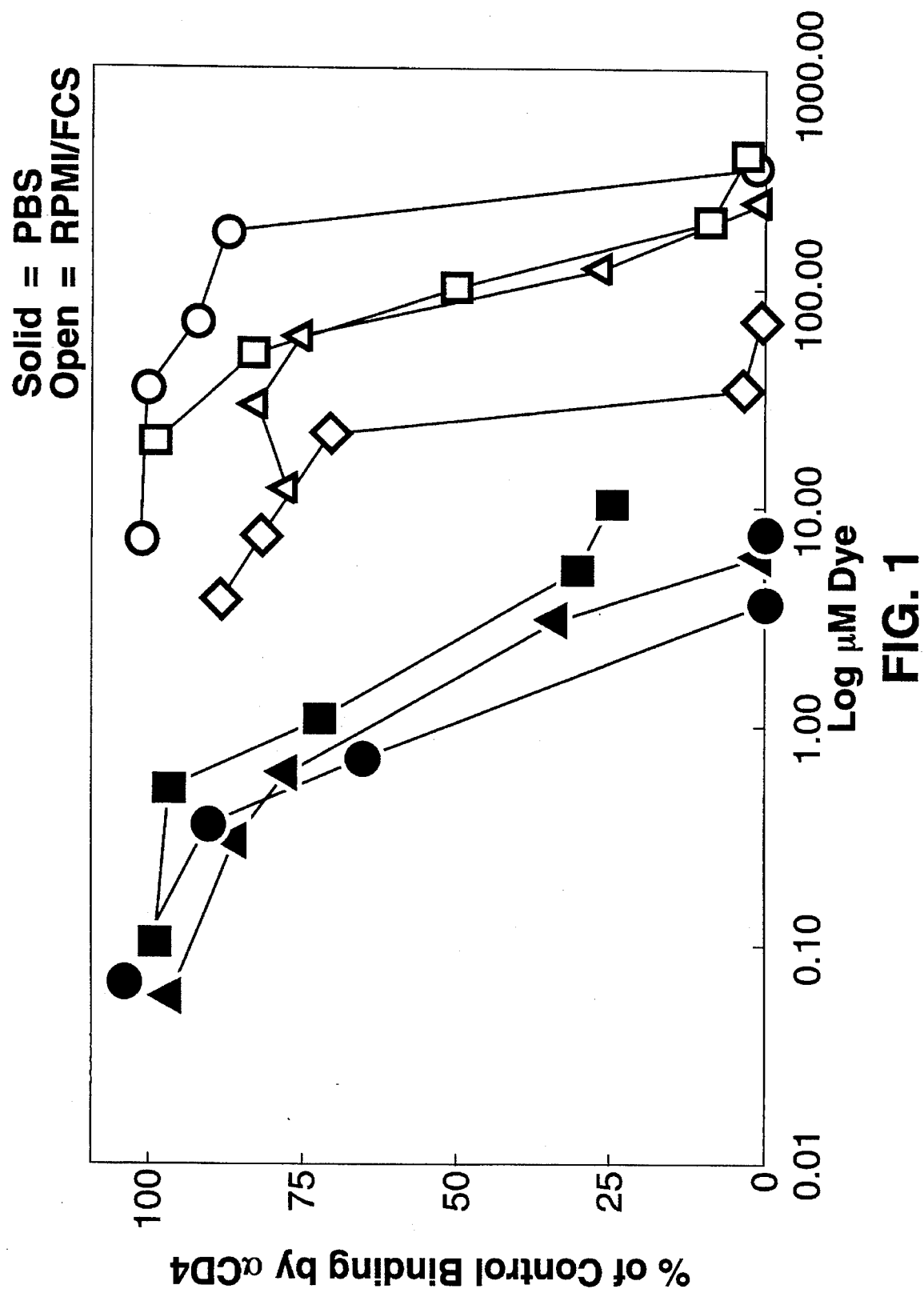
FIG. 1 is a graph showing the dose-response in the presence and absence. of serum proteins of the azo dye-mediated inhibition of binding of αCD4-FITC to CD4.

The present invention concerns pharmaceutical compositions containing particular azo dyes, as well as the use of such azo dyes in inhibiting the binding of a virus to CD4 glycoprotein, in protecting against or treating viral infections, and in detecting or quantitating CD4-positive T4 lymphocytes.

The azo dyes employed in the present invention have the general structure indicated below:

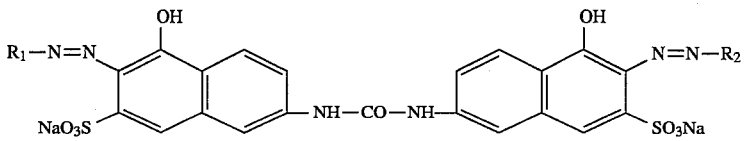

wherein $R_1$ and $R_2$ are individually benzene or napthalene which are independently non-, mono-, or disubstituted with OH, NaOOC, NHCOZ, $SO_3Na$, Z, or OZ, where Z is an alkyl group. The azo dyes utilized in the context of the present invention are preferably Direct Orange 26, which possesses benzyl groups at $R_1$ and $R_2$; Direct Red 23, which contains a benzyl group at $R_1$ and a methylcarboxyamido benzyl group at $R_2$; Direct Red 24, which consists of 2-methylbenzene sulfonic acid at $R_1$ and a methoxybenzyl group at $R_2$; and Direct Red 26, which has a methoxybenzyl group at $R_1$ and napthalene sulfonic acid at $R_2$. The dyes of the present invention may be further substituted, i.e., at positions other than $R_1$ and $R_2$, so long as such substitutions do not interfere with the desirable function of the azo dyes in the context of the present invention. Moreover, the present invention further contemplates the use of therapeutically acceptable derivatives and salts of the aforementioned azo dyes.

The azo dyes contemplated in the context of the present invention, including those preferred azo dyes identified above, are known compounds. Information on how to obtain and/or prepare these azo dyes is set forth in the *Colour Index* (3rd ed), 4, Society of Dyers and Colourists (Yorkshire BD1-2JB, England (1980)). The azo dye derivatives employed in the present invention may be used in the form of their pharmaceutically acceptable salts, may be used alone or in appropriate association, and also may be used in combination with other pharmaceutically active compounds. The pharmaceutically acceptable excipients described herein, for example, vehicles, adjuvants, carriers or diluents, are readily available to the public.

The azo dyes to be used in the present invention share the property of binding to a site on the CD4 glycoprotein molecule which is also recognized by the HIV coat protein gp120. Consequently these azo dyes may be employed in accordance with the present invention to inhibit the binding of viruses, such as members of the HTLV family including HTLV I, HTLV II, HTLV IV, HTLV V, HIV-1, and HIV-2, to their receptor, i.e., CD4 glycoprotein on T4 lymphocytes. By inhibiting the binding of the viruses to CD4, the viruses become incapable of infecting the cells. Thus the azo dyes can be used as effective antiviral agents.

The present invention includes pharmaceutical compositions comprising a pharmaceutically acceptable excipient and one or more of the aforementioned azo dyes as an active agent. The active agent may be present in the pharmaceutical composition in any suitable quantity.

The present invention also includes a method of inhibiting the binding of a virus to CD4-positive T4 lymphocytes by contacting T4 lymphocytes with one or more of the aforementioned azo dyes as an active agent. Moreover, by doing so in vivo, the present invention further provides a method of treating or protecting against the viral infection of mammalian cells by administering to a mammal, or contacting mammalian cells, with a therapeutically effective amount of one of the aforementioned azo dyes as an active agent. The present inventive method of protecting against or treating a viral infection is particularly well-suited with respect to retroviruses, especially HIV, in mammals such as humans.

Thus, while the method of the present invention can be practiced in vitro, it has particular usefulness in in vivo applications, and the inhibition of binding to CD4 has particular utility in, for example, the in vivo treatment of AIDS and AIDS-related complex, herpes, or other retroviral infections. As regards these applications, the present inventive method includes the administration to an animal, particularly a human, of a therapeutically effective amount of one or more of the aforementioned azo dyes as an active agent effective in the treatment or prevention of viral infections, particularly an active agent selected from the group consisting of Direct Orange 26, Direct Red 23, Direct Red 24, Direct Red 26, and pharmaceutically acceptable derivatives and salts thereof.

One skilled in the art will appreciate that suitable methods of administering a compound of the present invention to an animal are available, and, although more than one route can be used to administer a particular compound, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. However, pharmaceutically acceptable excipients capable of interacting with a T cell receptor are preferred.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the azo dye derivatives employed in the present invention may be made into suppositories by mixing with a variety of bases such as emulsifying bases or water-soluble bases.

Formulations suitable for vaginal administration may be presented as pessaries, tampons, creams, gels, pastes, foams, or spray formulas containing, in addition to the active ingredient, such carriers as are known in the art to be appropriate.

The dose administered to an animal, particularly a human, in the context of the present invention should be sufficient to effect a prophylactic or therapeutic response in the animal over a reasonable time frame. One skilled in the art will recognize that dosage will depend upon a variety of factors including the strength of the particular compound employed, the condition of the animal, the body weight of the animal, as well as the severity of the infection and stage of the disease. The size of the dose will also be determined by the existence, nature, and extent of any adverse side-effects that might accompany the administration of a particular compound. Suitable doses and dosage regimens can be determined by comparisons to antiviral agents (such as AZT and ddI) known to effect the desired antiviral response. Specifically, a suitable dose is that which will result in a concentration of the active agent (in blood and/or tissues harboring virus) which is known to inhibit the virus, e.g., about 1–100 µM, and more preferably about 8–80 µM, particularly of Direct Orange 26. The preferred dosage is the amount which results in the greatest reduction in viral titer, without significant side effects. In proper doses and with suitable administration of certain compounds, the present invention provides for a wide range of the inhibition of viral proliferation, e.g., from little inhibition to essentially full inhibition.

The azo dye compositions of the present invention may also be utilized in a diagnostic method for assaying for CD4-positive T4 lymphocytes. In this diagnostic method, the capability of such compounds to bind to the CD4 glycoprotein of T4 lymphocytes can be employed. For example, this ability can be exploited in an assay used to define the subset of T4 lymphocytes which are CD4+, or used to monitor lymphocytic cell maturation, as CD4 was originally characterized as a T lymphocyte differentiation antigen (Lifson et al., supra).

Such detection assays will typically involve: (a) contacting a sample suspected of containing T4 lymphocytes with an azo dye of the present invention under conditions (e.g. appropriate temperature and amount of time for binding) sufficient to ensure binding between the azo dye and T4 lymphocytes which may be present in the sample; (b) removing unbound active agent from the sample; and (c) detecting the presence of active agent in the sample by any suitable means as indicative of the presence of T4 lymphocytes. This method may be extended to include quantifying the bound active agent by any suitable means, and correlating the quantity of bound active agent to the quantity of T4 lymphocytes in the sample. Some examples of suitable means of quantitating bound active agent include spectrophotometric detection, detection using an antibody directed to the azo dye, and quantitation of radiolabeled azo dyes. It is also possible that certain uses of the azo dye may not require removal of unbound dye, an example being the case where an antibody is available which recognizes the bound, but not the unbound form of the azo dye.

The following examples further illustrate the present invention and should not be construed as in any way limiting its scope.

Example 1

This example confirms the ability of the azo dyes contemplated for use in connection with the present invention to inhibit binding to CD4 by viruses. Human peripheral blood lymphocytes (PBL) were used to support virus replication and to test the antiviral effects of the azo dyes since PBL provide a reasonable model for the in vivo condition (Anand et al., *AIDS Res. Human Retrovir.*, 6, 679–689 (1990)).

Since anti-Leu3a (αCD4) and recombinant HIV coat protein (rgp120) bind to the same site on the CD4 molecule, interference in binding of CD4 confirms interference in HIV binding to αCD4 (Weaver et al., *AIDS Res. Human Retrovir.*, 6, 1125–1130 (1990)). For these binding assays, PBL were prepared by density gradient centrifugation, and the effect of the azo dyes on the binding of anti-CD4-FITC (Becton Dickinson, Mountain View, Calif.) was measured (Weaver et al., supra). Cells were treated with an azo dye for at least 10 minutes at room temperature, or for more than 30 minutes at 4° C., and were then contacted with FITC-labeled antibody. Binding was measured by quantitating cell bound fluorescence using flow cytometry.

The following azo dyes were utilized in this experiment: Direct Orange 26 (Colour Index #29150), Direct Red 23 (Colour Index #29160), Direct Red 24 (Colour Index #29185), and Direct Red 26 (Colour Index #29190) (Food and Drug Administration, Washington, D.C.). Evans blue (EB; Sigma Chemical Co., St. Louis, Mo.) was used as a positive control since it has been shown previously to block αCD4 and rpg120 binding (Weaver et al., *AIDS Res. Human Retrovir.*, 6, 1125–1130 (1990)).

Confirmation of the ability of the azo dyes Direct Orange 26, Direct Red 23, Direct Red 24, and Direct Red 26 to interfere with binding of αCD4 to PBL, as well as results obtained using Evans Blue, are presented in Table 1.

TABLE 1

| Dye-mediated inhibition of binding of αCD4 to PBL. | | |
|---|---|---|
| Compound | Concentration | % Control Binding[1] |
| Evans Blue | 1 µM | 1 |
| Direct Orange 26 | 10 µM | 0 |
| Direct Red 23 | 20 µM | 0 |
| Direct Red 24 | 20 µM | 0 |
| Direct Red 26 | 20 µM | 0 |

[1]Results in % logarithmic mean channel number of αCD4-FITC binding in PBS

The results in Table 1 verify that 10 µM of Direct Orange 26 and 20 µM of Direct Red 23, Direct Red 24, and Direct Red 26 completely inhibited the binding of αCD4 to CD4. These results corroborate that the azo dyes contemplated for use in connection with the present invention are quite effective in inhibiting the binding of viruses to the CD4 receptor.

Example 2

This example further demonstrates the ability of the azo dyes contemplated for use in connection with the present invention to inhibit binding to CD4 by viruses, in particular to inhibit the binding of HIV rgp120 to CD4.

The ability of Direct Orange 26, Direct Red 23, Direct Red 24, and Direct Red 26 to inhibit the binding of HIV rgp120 to CD4 was determined using monoclonal anti-rgp120-FITC (Genentech, Inc., San Francisco, Calif.) to detect recombinant HIV coat protein in the binding assay described in Example 1.

Confirmation of the efficacy of these agents in blocking the binding of rgp120 to the CD4 receptor is presented in Table 2. It can be seen that these agents were each effective at about the same concentration, namely 2.5–5.0 μM.

TABLE 2

Dye-mediated inhibition of HIV rgp120 binding

| Compound | Concentration | % Control Binding[1] |
|---|---|---|
| Evans Blue | 1 μM | 8 |
| Direct Orange 26 | 1 μM | 26 |
| Direct Orange 26 | 2.5 μM | 15 |
| Direct Red 23 | 5.0 μM | 10–15 |
| Direct Red 24 | 5.0 μM | 10–15 |
| Direct Red 26 | 5.0 μM | 10–15 |

[1]Results in % logarithmic mean channel number of rgp120 binding detected by binding of αrgp120-FITC in PBS Example 3

This example substantiates the specificity of the azo dyes used in the context of the present invention to inhibit CD4 binding.

The specificity of the dyes was confirmed by testing their ability to interfere with the binding of two other monoclonal antibodies, αCD3 and αCD8, to PBL using the binding assay described in Example 1.

Validation of the specificity of the azo dyes for CD4 is presented in Table 3, using Direct Orange 26 as an example. Similar specificity results were obtained for Direct Red 23, Direct Red 24, and Direct Red 26. It can be seen in Table 3 that the azo dyes completely abolished binding of αCD4, had no effect on binding of αCD3, and minimally reduced binding of αCD8 to PBL.

TABLE 3

Specificity of inhibition of binding of monoclonal antibodies by dyes

| | | % Control Binding[1] | | |
|---|---|---|---|---|
| Compound | Concentration | αCD4 | αCD3 | αCD8 |
| Evans Blue | 1 μM | 1 | — | — |
| Direct Orange 26 | 10 μM | 0 | 103 | 65 |

[1]Results in % logarithmic mean channel number of αCD4-FITC, αCD3-FITC, or αCD8-FITC binding in PBS Example 4

This example confirms the absence of significant binding of the azo dyes used in the context of the present invention to serum proteins, as compared to other azo dyes which have been previously described.

Using the binding assay described in Example 1, the dose-response curves for the azo dyes in the presence (phenol red free RPMI 1640 with 5% serum) and absence (PBS; phosphate buffered saline) of serum were obtained to verify the absence of substantial binding of the dyes contemplated in the present invention to serum proteins. For comparison purposes, some of the dyes described in U.S. patent application Ser. No. 07/684,258, namely Acid Red 115 (Colour Index #27200) (Sandoz, Inc.), Direct Red 79 (Colour Index #29065) (Sandoz, Inc.), and Acid Blue 116 (Colour Index #26380) (Matheson Coleman Co., E. Rutherford, N.J.), were also examined.

The dose response curves for the azo dyes are set forth in FIG. 1, which presents data for Direct Orange 26 that is representative of similar data obtained for Direct Red 23, Direct Red 24, and Direct Red 26. The solid symbols indicate incubation in PBS, and the open symbols indicate incubation in complete cell culture medium (RPMI 1640 with 5% serum). Diamonds represent Direct Orange 26; circles represent Acid Blue 116; triangles represent Acid Red 115; and squares represent Direct Red 79.

FIG. 1 corroborates the effectiveness of all of the dyes at inhibiting αCD4 binding to PBL in the presence of buffer. In the presence of serum, however, about 100× more of the comparative azo dyes Acid Red 115, Direct Red 79, and Acid Blue 116 was needed for efficacy, due to the binding of these dyes to serum proteins.

In comparison, in the presence of serum, only about 5× more of Direct Orange 26 was needed to inhibit αCD4 binding. These results validate the superiority of the azo dyes described in the present invention over those described previously in terms of their ability to inhibit binding to CD4 in the presence of serum proteins.

Example 5

This example verifies the lack of a significant adverse effect on cell viability as a consequence of contact with the azo dyes used in the context of the present invention.

The absence of a substantial negative effect of the azo dyes on cell viability was corroborated by culturing PBL for 72 hours at 37° C. in the presence of 1 μl/ml of anti-T-cell receptor antibody (αTCR). Cells were then washed once in PBS, and resuspended in PBS with 3 μg/ml propidium iodide. After 10 minutes incubation, the cells were analyzed by flow cytometry. Live cells were defined as those excluding propidium iodide.

Experimental results set forth in Table 4 verify that Direct Orange 26 has only a slight negative effect on lymphocyte proliferation. Specifically, the azo dye reduced viability by at most 10%. Similar viability results were obtained for Direct Red 23, Direct Red 24, and Direct Red 26.

TABLE 4

Effect of Direct Orange 26 on viability of PBL after 72 hour culture of αTCR stimulation

| Treatment | Concentration | % Viable Cells[1] |
|---|---|---|
| None | — | 78.2 |
| Direct Orange 26 | 400 μM | 67.5 |
| Direct Orange 26 | 800 μM | 71.5 |

[1]Viability determined by ability to exclude propidium iodide as measured by flow cytometry

Example 6

This example confirms the ability of the azo dyes contemplated for use in the context of the present invention to inhibit HIV replication.

The ability of the azo dyes to negatively affect HIV replication was verified after six days of culturing the HIV isolate LAV-$1_{BR}$ in phytohemagglutinin-stimulated human PBL. For this experiment, the amount of intracellular HIV p24 protein in cell lysates was quantitated with use of an HIV p24 enzyme linked immunosorbent assay kit (Cellular Products, Buffalo, N.Y.) as described in Anand et al., *AIDS Res. Human Retrovir.*, 6, 679–689 (1990). This measure of p24 protein was considered an indication of HIV replication. Aurintricarboxylic acid (ATA; Sigma Chemical Co., St. Louis, Mo.) was included in this experiment as a positive control, and the solvent DMSO was utilized for further comparative purposes.

The results of this experiment are set forth in Table 5 and substantiate that Direct Orange 26 is clearly able to strongly decrease HIV replication. While the table sets forth results obtained with Direct Orange 26, similar inhibitory effects of the drugs on HIV replication were observed for Direct Red 23, Direct Red 24, and Direct Red 26 when these agents were used at concentrations of 50–80 µg/ml.

TABLE 5

Effect of Direct Orange 26 on growth of HIV in vitro

| Treatment | Concentration | pg/ml HIV p24 |
| --- | --- | --- |
| Cells only | — | 0 |
| Virus only | — | 101,000 |
| ATA | 50 µg/ml | 1 |
| Direct Orange 26 | 50 µg/ml | 71 |
| Direct Orange 26 | 100 µg/ml | 61 |
| DMSO | 100 µg/ml | 50,000 |

All of the references cited herein are hereby incorporated in their entireties by reference.

While this invention has been described with an emphasis on preferred embodiments, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed is:

1. A diagnostic method for detecting CD4-positive T4 lymphocytes in a sample, which method comprises:

contacting a sample with a compound having the formula:

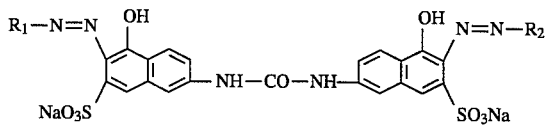

and pharmaceutically acceptable salts thereof, wherein $R_1$ and $R_2$ are individually benzene or naphthalene which are independently non-, mono-, or disubstituted with OH, NaOOC, NHCOZ, $SO_3Na$, Z, or OZ, wherein Z is an alkyl group, under sufficient conditions to allow binding of said T4 lymphocytes and said compound, removing unbound compound from said sample, and detecting the presence of compound in said sample as indicative of the presence of T4 lymphocytes.

2. The method of claim 1, wherein said compound is selected from the group consisting of Direct Orange 26, Direct Red 23, Direct Red 24, and Direct Red 26.

3. The method of claim 2, wherein said compound is Direct Orange 26.

4. The method of claim 1, which method further comprises quantifying said bound compound and correlating the quantity of bound compound to the quantity of T4 lymphocytes in said sample.

5. A method of inhibiting the binding of a human immunodeficiency virus to a CD4 glycoprotein of a T4 lymphocyte, which method comprises contacting said T4 lymphocyte with an amount effective at inhibiting the binding of said virus to the CD4 glycoprotein of said T4 lymphocyte of a compound having the formula:

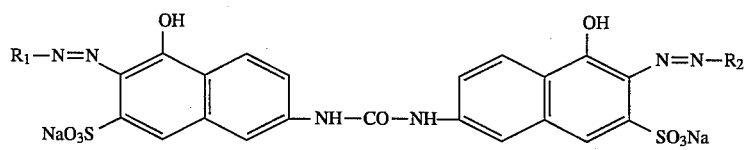

and pharmaceutically acceptable salts thereof, wherein $R_1$ and $R_2$ are individually benzene or naphthalene which are independently non-, mono-, or disubstituted with OH, NaOOC, NHCOZ, $SO_3Na$, Z, or OZ, wherein Z is an alkyl group.

6. The method of claim 5, wherein said compound is selected from the group consisting of Direct Orange 26, Direct Red 23, Direct Red 24, and Direct Red 26.

7. The method of claim 6, wherein said compound is Direct Orange 26.

8. The method of claim 5, wherein said T4 lymphocyte is contacted with said compound in a pharmaceutically acceptable excipient.

9. The method of claim 5, wherein said contacting occurs in vitro.

10. The method of claim 9, wherein said compound is selected from the group consisting of Direct Orange 26, Direct Red 23, Direct Red 24, and Direct Red 26.

11. The method of claim 10, wherein said compound is Direct Orange 26.

12. The method of claim 5, wherein said contacting is carried out in the presence of serum protein.

13. The method of claim 12, wherein said compound is selected from the group consisting of Direct Orange 26, Direct Red 23, Direct Red 24, and Direct Red 26.

14. The method of claim 12, wherein said contacting occurs in vitro.

15. The method of claim 13, wherein said contacting occurs in vitro.

* * * * *